(12) United States Patent
Wu et al.

(10) Patent No.: US 6,365,102 B1
(45) Date of Patent: Apr. 2, 2002

(54) METHOD OF ENHANCED STERILIZATION WITH IMPROVED MATERIAL COMPATIBILITY

(75) Inventors: Su-Syin S. Wu, Irvine; Nancy S. Chu, Laguna Niguel; Abraham Merhazion, Tustin, all of CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

(21) Appl. No.: 09/470,246

(22) Filed: Dec. 22, 1999

Related U.S. Application Data
(60) Provisional application No. 60/127,160, filed on Mar. 31, 1999.

(51) Int. Cl.[7] .............................. A61L 2/14; A61L 2/16
(52) U.S. Cl. .............................. 422/23; 422/28; 422/33
(58) Field of Search ........................... 204/164; 422/23, 422/33, 186.05, 186.23, 186.25; 34/257

(56) References Cited

U.S. PATENT DOCUMENTS

| | | | |
|---|---|---|---|
| 2,972,196 A | 2/1961 | Early et al. | |
| 4,335,071 A | * 6/1982 | Thornton | 422/26 |
| 4,348,357 A | 9/1982 | Bithell | 422/22 |
| 4,643,876 A | 2/1987 | Jacobs et al. | 422/23 |
| 4,756,882 A | 7/1988 | Jacobs et al. | 422/23 |
| 4,818,488 A | 4/1989 | Jacob | 422/23 |
| 5,084,239 A | 1/1992 | Moulton et al. | 422/23 |
| 5,186,893 A | 2/1993 | Moulton et al. | 422/23 |
| 5,244,629 A | 9/1993 | Caputo et al. | 422/22 |
| 5,288,460 A | 2/1994 | Caputo et al. | 422/23 |
| 5,413,758 A | 5/1995 | Caputo et al. | 422/22 |
| 5,527,508 A | 6/1996 | Childers et al. | 422/33 |
| 5,645,796 A | 7/1997 | Caputo et al. | 422/22 |
| 5,656,238 A | 8/1997 | Spencer et al. | 422/23 |
| 5,869,000 A | 2/1999 | DeCato | 422/33 |
| 6,060,019 A | * 5/2000 | Spencer et al. | 422/23 |

FOREIGN PATENT DOCUMENTS

EP     0 707 186 A1     4/1996     .............. F26B/5/00

OTHER PUBLICATIONS

A New Technology for Instrument Sterilization, Advanced Sterilization Products, Paul T. Jacobs, 1993.

* cited by examiner

Primary Examiner—Margaret G. Moore
Assistant Examiner—Michael J Feely
(74) Attorney, Agent, or Firm—Knobbe, Martens, Olson & Bear, LLP

(57) ABSTRACT

A method of enhanced sterilization with improved material compatibility. The following enhancements have been made. First, repeated venting, evacuation, and plasma treatments can be performed in the pre-plasma stage. Second, a lower power level can be used in the post-plasma stage than in the pre-plasma stage. Third, after the post-plasma stage, the chamber can be held at atmospheric pressure or sub-atmospheric pressure for a period of time after venting, before re-evacuating the chamber, rather than evacuating after the chamber is vented to atmospheric pressure or sub-atmospheric pressure. Any of the three enhancements may be used separately, and it is not necessary to practice all three enhancements to obtain at least some of the benefits of enhanced sterilization with improved material compatibility.

24 Claims, 6 Drawing Sheets

METHOD OF ENHANCED STERILIZATION WITH IMPROVED MATERIAL COMPATIBILITY

RELATED APPLICATIONS

This application claims the benefits under 35 U.S.C. §119(e) of Provisional Application No. 60/127,160, filed Mar. 31, 1999.

BACKGROUND OF THE INVENTION

1. Field of the Invention

This invention relates to a method of enhancing sterilization with a sterilant vapor and plasma with improved material compatibility.

2. Description of the Related Art

Some new commercial systems for sterilizing medical instruments and the like utilize low-temperature reactive gas plasma to achieve rapid, low-temperature, low-moisture sterilization of medical items. Low-temperature gas plasma is sometimes described as a reactive cloud which may contain ions, electrons, and/or neutral atomic particles. This state of matter can be produced through the action of electric or magnetic fields, or through other external forces such as high-energy particle flux. In general, an electric field can be in any frequency range (an example of a naturally occurring plasma is the aurora borealis or the northern lights). One commercial embodiment of plasma sterilization is the STERRAD® Sterilization Process, as described in U.S. Pat. No. 4,643,876.

The STERRAD Sterilization Process is performed in the following manner. The items to be sterilized are placed in the sterilization chamber, the chamber is closed, and a vacuum is drawn. An aqueous solution of hydrogen peroxide is injected and vaporized into the chamber so that it surrounds the items to be sterilized. After reduction of the pressure in the sterilization chamber, a low-temperature gas plasma is initiated by applying radio frequency energy to create an electrical field. In the plasma, the hydrogen peroxide vapor is dissociated into reactive species that collide/react with and kill microorganisms. After the activated components react with the organisms or with each other, they lose their high energy and recombine to form oxygen, water, and other nontoxic byproducts. The plasma is maintained for a sufficient time to achieve sterilization and remove residuals. At the completion of the process, the RF energy is turned off, the vacuum is released, and the chamber is returned to atmospheric pressure by the introduction of High Efficiency Particulate-Filtered Air (HEPA).

The above-described sterilization system can safely process medical items currently sterilized by ethylene oxide and steam, with the exception of linens and other cellulosic materials, powders, and liquids. Sterilized items are ready to be used in a little over an hour after starting the sterilizer. The process requires no aeration, and there are no toxic residues or emissions. Preparation of instruments for sterilization is similar to current practices: cleaning the instruments, reassembly, and wrapping. The system typically uses non-woven polypropylene wraps or sterilization pouches made of at least one permeable side, both of which are commercially available, and a tray and container system. A special vessel containing liquid sterilant can be placed on long, narrow lumen instruments to allow rapid sterilization of their channels. A chemical indicator specifically formulated for this process is used, as well as a specifically designed biological indicator test pack.

The efficacy of the STERRAD Plasma sterilization system has been demonstrated. Depending upon the particular design, plasma sterilization systems can therefore provide efficient, safe methods for sterilizing medical instruments and other hospital products.

For optimum operation, a plasma sterilization system such as that described above requires the loads that are to be sterilized to be quite dry. However, normal hospital practice in the preparation of instruments for sterilization often results in levels of water that may be excessive. The excess water makes it difficult to achieve the low-pressure thresholds required to initiate the sterilization process. To initiate the sterilization process, the chamber pressure is preferably reduced to relatively low levels, for example approximately 200–700 mTorr. Since the equilibrium vapor pressure of water is significantly higher than 700 mTorr at room temperature, any water in the chamber or load will begin to vaporize during the vacuum phase. The heat of vaporization required for the water to vaporize causes the load and any remaining water to chill. When enough water has vaporized, the remaining liquid begins to freeze. Eventually, the remaining liquid will completely freeze, which slows the rate of vapor generation and retards the attainment of the pressure levels required for optimum operation of the sterilizer. These conditions can cause undesirably long sterilization cycles or even cancellation of the sterilization cycle. Spencer et al. (U.S. Pat. No. 5,656,238) disclosed that plasma can be used to enhance the drying so that the desired pressure for sterilization may be achieved more quickly.

Improper plasma treatment can lead to damage to materials in the chamber or in the equipment, however. There is a need for a method of enhancing material compatibility while simultaneously achieving high sterilization efficiency.

SUMMARY OF THE INVENTION

One aspect of the invention involves a method of sterilizing articles in a load in a chamber with a chemical sterilant. The method includes conditioning the load, then introducing chemical sterilant; and maintaining to achieve sterilization. Conditioning the load includes evacuating the chamber, generating plasma in the chamber, venting the chamber to approximately atmospheric or subatmospheric pressure, and repeating the evacuating, generating plasma, and venting at least two times.

Preferably, conditioning the load includes increasing the temperature of at least a portion of the load to at least 30° C. Advantageously, conditioning the load comprises increasing the temperature of at least a portion of the load to at least 35° C. In a preferred embodiment, the chemical sterilant is hydrogen peroxide.

Advantageously, plasma is generated in the chamber when the sterilant is introduced or during the maintaining. Preferably, the method also includes venting the chamber to a pressure, maintaining the pressure, and then evacuating the chamber, where the venting is after the maintaining. Advantageously, the plasma generated during the introducing of the sterilant or the maintaining is generated with lower power than the plasma generated after conditioning and evacuating.

Another aspect of the invention involves a method of reducing sterilant residuals on articles in a load in a chamber. The method includes evacuating the chamber a first time, introducing sterilant, maintaining to achieve sterilization, venting the chamber to a pressure, maintaining the pressure, evacuating the chamber a second time, venting the chamber a second time, and removing the articles in the load from the chamber.

Advantageously, the venting pressure is atmospheric or sub-atmospheric pressure. Preferably, plasma is generated in the chamber during the introducing of the sterilant, during maintaining, or evacuating a second time.

Advantageously, the venting, maintaining, and evacuating a second time are repeated. Preferably, the chamber is evacuated, plasma is generated, and the chamber is vented before the method of reducing process residuals is carried out.

Yet another aspect of the invention involves a method for sterilizing devices in a chamber, where the method includes at least two plasma steps, where at least one plasma step occurs before introducing the chemical sterilant and at least one plasma step occurs after introducing the chemical sterilant. The method includes generating plasma with a higher power level in the plasma step occurring before the chemical sterilant is introduced than in the plasma step occurring after the chemical sterilant is introduced.

Preferably, the chemical sterilant is hydrogen peroxide. Advantageously, the method also includes venting the chamber and evacuating the chamber after generating plasma with the higher power level.

In an embodiment, the method also includes venting the chamber to a pressure, maintaining the pressure, and evacuating the chamber, where the venting, maintaining, and evacuating occur after the plasma step occurring after the chemical sterilant is introduced.

Another aspect of the invention involves a method of sterilizing articles in a load with a chemical sterilant in a chamber with improved material compatibility. The method involves evacuating the chamber, generating plasma with a first power level, venting the chamber to a pressure, evacuating the chamber, and introducing chemical sterilant into the chamber. Introducing the sterilant occurs after generating plasma with the first power level. The chamber is evacuated, plasma with a second power level is generated, where the plasma with the second power level is generated after the sterilant is introduced. The method also includes venting the chamber, where the venting occurs after generating plasma with the second power level. The chamber is then evacuated and vented. The first power level is higher than the second power level, thereby sterilizing the articles with improved material compatibility. Advantageously, the chemical sterilant is an antimicrobial agent. Preferably, the antimicrobial agent is hydrogen peroxide.

Advantageously, evacuating, generating plasma with the first power level, and venting is repeated more than once. Preferably, the chamber is venting after the chemical sterilant is introduced into the chamber Advantageously, the pressure is maintained after venting. In an embodiment, additional plasma is generated in the chamber after generating plasma with the second power level, venting, and evacuating. Advantageously, the venting and evacuating are repeated.

DETAILED DESCRIPTION OF THE PREFERRED EMBODIMENT

Figure 1:
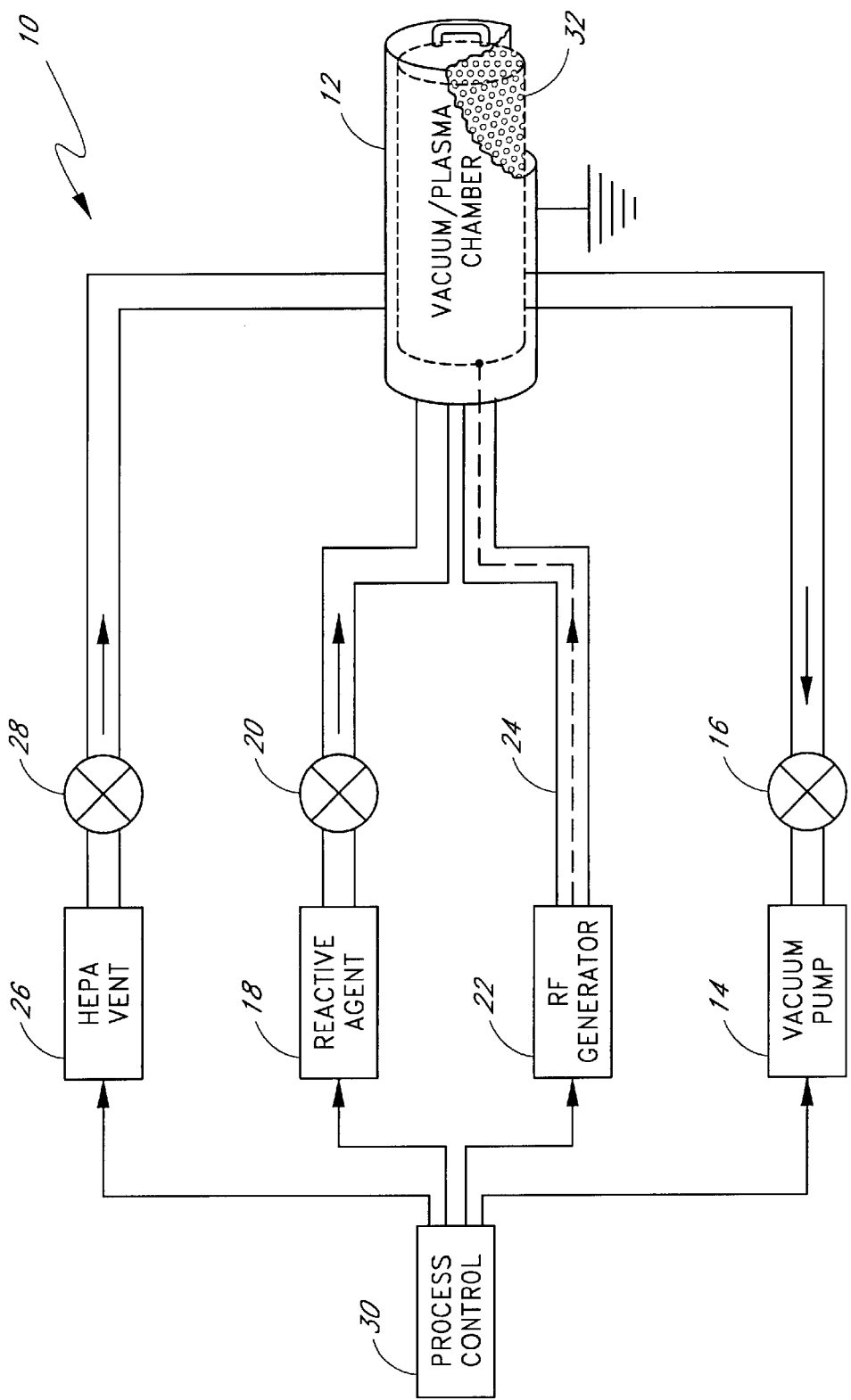
FIG. 1 is a simplified diagram of a sterilization apparatus.

Referring to the drawings, FIG. 1 depicts a sterilizer in block diagram form generally at 10. The sterilizer 10 and its components and methods of use are described more fully in U.S. Pat. 4,756,882, issued Jul. 12, 1988. This patent is incorporated by reference herein. Other sterilizers are suitable for the method of the invention, and the sterilizer of FIG. 1 is not meant to be limiting to the method. The sterilizer 10 includes a vacuum chamber 12, a vacuum pump 14 connected to the vacuum chamber 12 by a valve 16, and a source of suitable reactive agent 18 such as hydrogen peroxide connected to the vacuum chamber 12 by a line having a valve 20 therein. The sterilizer 10 also includes an RF generator 22 electrically connected to the plasma generator inside the vacuum chamber 12 by a suitable coupling 24, as well as a HEPA vent 26 connected to the vacuum chamber via a line and a valve 28. A process control logic 30, preferably a programmable computer, is connected to each of the components which are connected to the vacuum chamber 12. The process control logic 30 directs the operation of each of the components connected to the vacuum chamber at the appropriate time to effectuate the sterilization operation.

The vacuum chamber 12 contains the objects to be sterilized and is sufficiently gas-tight to support a vacuum of less than 300 mTorr. Inside the chamber 12 is an RF antenna, or electrode array 32 to which the RF energy is supplied. In one preferred embodiment the electrode is arranged such that it is tubular and equidistant from the chamber 12 wall to produce a symmetric RF electric field distribution. In another embodiment, the electrode and chamber are in a rectangular shape so as to provide more usable space. The electrode excites a plasma when an RF potential is applied by the RF generator 22 through the RF coupling 24. The RF coupling 24 may be a coaxial cable or other such waveguide capable of transmitting high power RF energy without significant impedance loss connected to an impedance matching device for the electrode.

The vacuum pump 14 and connecting valve 16 comprise a conventional arrangement well known in the art. The vacuum pump is typically a mechanical vacuum pump such as the rotary vane variety, capable of drawing a vacuum in the dry vacuum chamber 12 of approximately 300–1500 mTorr or less within approximately 5 minutes of pumping. The valve 16 should have sufficient integrity to seal a vacuum of less than 300 mTorr without significant leakage. This requirement also applies to the other valves 20 and 28 present in the sterilizer.

The RF generator 22 is a conventional oscillator well known in the art, such as for example a solid-state or a vacuum tube oscillator with power amplification. The combination may generate energy in a frequency range of 0.1 MHz to 30 MHz and powers ranging from 50 W to 1500 W, and preferably a frequency of 13.56 MHz and power greater than 100 W.

Figure 2:
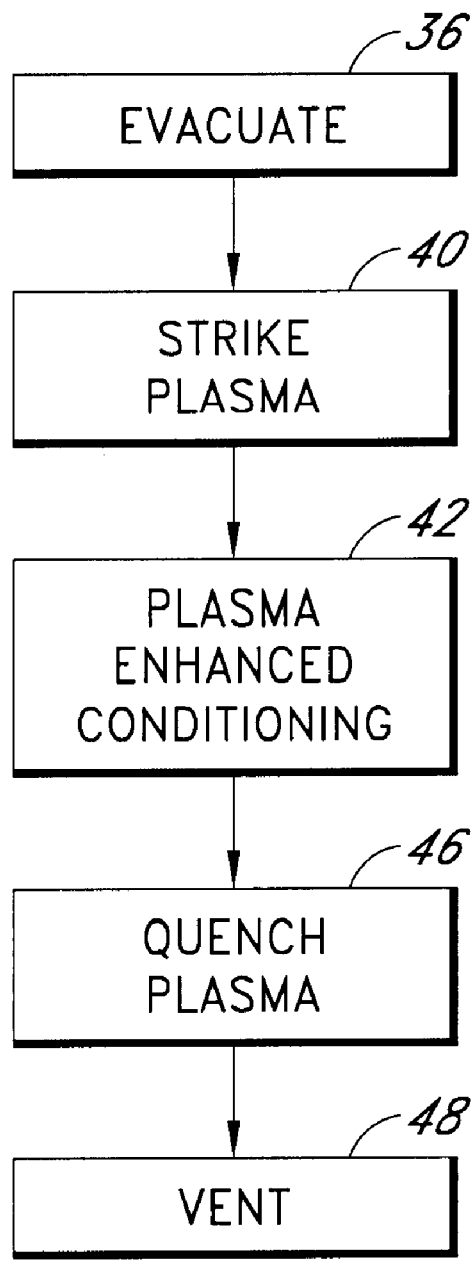
FIG. 2 is a block diagram of a plasma enhanced conditioning process.
Figure 3:
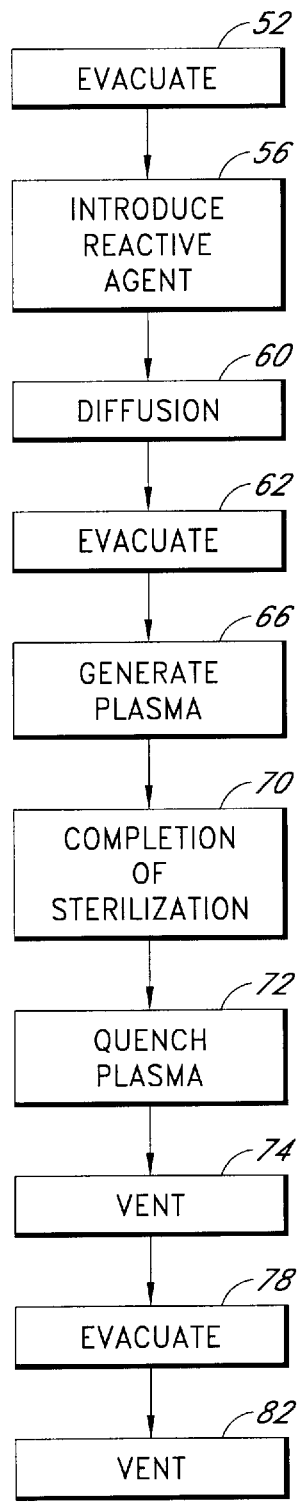
FIG. 3 is a block diagram of a sterilization process including the post-plasma treatment.
Figure 4:
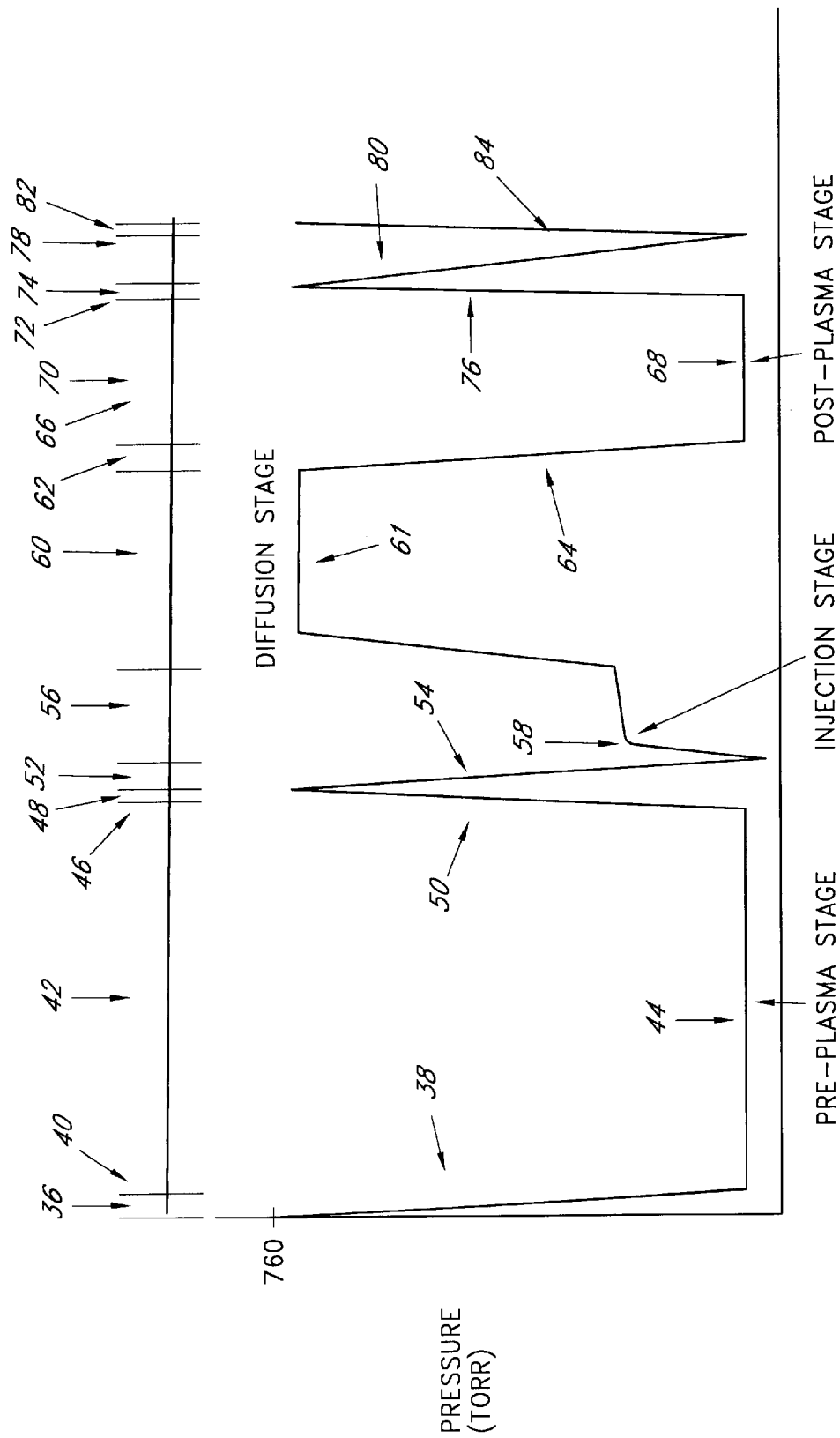
FIG. 4 is a pressure diagram of a sterilization process.

Operation of the sterilizer without the enhancements of the present invention is described in schematic form in FIGS. 2–4, where FIGS. 2 and 3 illustrate the sequence of operations in the sterilizer 10, and FIG. 4 illustrates the pressure in the chamber 12 as a function of time. The steps in FIG. 2 are mainly for conditioning the load, and the sterilization cycle starts from the steps listed in FIG. 3.

After the objects to be sterilized have been placed in the vacuum chamber and the chamber has been sealed, the process control logic 30 engages the vacuum pump 14 and valve 16 to evacuate the chamber, step 36 in FIG. 2. The pressure in the vacuum chamber is shown qualitatively as curve 38 in FIG. 4. The chamber is preferably evacuated to a pressure of less than or equal to 5000 mTorr, more preferably 200–2000 mTorr, and most preferably about 300–1500 mTorr.

When the desired pressure has been reached, the process control logic 30 transmits a signal to the RF generator 22 to energize the electrode 32 within the chamber 12. This action causes a gas plasma to be created inside the chamber comprised of residual gas species, step 40 of FIG. 2. Because the articles to be sterilized are loaded into the chamber in the presence of air and moisture, the residual gases at this stage are mainly air and moisture.

As described in U.S. Pat. No. 5,656,238, hereby incorporated by reference, energy is transferred to condensed water in the chamber, thereby aiding the drying of the chamber and the equipment in the chamber. While plasma is being generated, the vacuum pump 14 remains engaged to further evacuate the chamber and remove residual gases and moisture from the chamber. This step is labeled as plasma enhanced conditioning, step 42, in FIG. 2, and the pressure in the chamber is curve 44 of FIG. 4. After a period of time, approximately 1–60 minutes, more preferably 2–40 minutes and most preferably 5–20 minutes, the plasma generator is turned off or quenched, step 46 in FIG. 2. The plasma processing conditioning of step 42 has also been described as "pre-plasma", because the plasma process takes place before injection of the reactive agent 18 or sterilant. At this point in the process, the evacuation can be continued, or, alternatively, the chamber can be vented, step 48 of FIG. 2 and curve 50 of FIG. 4. It is generally preferred to vent the chamber, because the venting helps in the drying process. The chamber can be vented to atmospheric or subatmospheric pressure. In some embodiments, the chamber can be vented to a pressure higher than atmospheric pressure, though this is not preferred. The steps in FIG. 2 are optional steps to condition the load. If the load does not require conditioning, the cycle can be started from the sterilization steps shown in FIG. 3.

The sterilization cycle starts from step 52 of FIG. 3 and curve 54 of FIG. 4. The chamber is evacuated to a pressure less than or equal to 10,000 mTorr, more preferably 100–5000 mTorr, and most preferably 300–1000 mTorr. When the desired vacuum threshold has been reached, the reactive agent 18 or sterilization agent is injected in step 56 of FIG. 3. The injection of the sterilization agent during step 56 causes the pressure inside the chamber to rapidly rise. In the preferred embodiment, the pressure may rise to a level of approximately 3000 mTorr or more, as indicated by the curve 58 in FIG. 4. The sterilization agent is preferably aqueous hydrogen peroxide, though other sterilization agents such as anhydrous peroxide generated from solid peroxide complexes, chlorine dioxide, ozone, ethylene oxide, peracetic acid, and other agents can also be used. The injection phase takes approximately 1–60 minutes.

After the reactive agent or sterilization agent is injected into the chamber, it is allowed to diffuse completely and evenly throughout the chamber during the diffusion step 60 of FIG. 3. This step typically lasts approximately 1–300 minutes, at which time the sterilization agent should be substantially at equilibrium inside the chamber 12. Preferably, though optionally, the chamber is vented to atmospheric pressure during the diffusion stage, as shown by the pressure curve 61 of FIG. 4. Venting the chamber during the diffusion stage helps the sterilization process by more effectively transferring the heat to the load from the electrode and the chamber walls.

At the end of the diffusion period, the process control logic 30 again engages the vacuum pump 14 and opens the valve 16 to pump down the chamber 12 to a vacuum less than or equal to 5000 mTorr, more preferably 200–2000 mTorr, and most preferably 200–1500 mTorr during step 62 of FIG. 3. The pressure during the evacuation after the diffusion step is shown as curve 64 in FIG. 4. When the pressure inside the chamber 12 has reached the desired pressure, the process control logic 30 commands the RF generator 22 to generate an RF signal which is transmitted to the plasma generator. This action causes a gas plasma to be generated inside the chamber 12 during step 66 of FIG. 3.

Generating the plasma induces a brief rise in pressure. This brief rise in pressure is not shown in FIG. 4, where the pressure curve dulling step 66 is labeled as curve 68. The plasma stage after injection of the reactive agent is called the post-plasma stage, because the plasma is generated after the injection of the reactive agent. The plasma generator remains energized for approximately 1–60 minutes. Both the plasma generation step 66 and the sterilization step 70 of FIG. 3 are included in pressure curve 68 of FIG. 4.

Referring to FIG. 3, maintaining to achieve sterilization may only include steps 60 and 70, diffusion and completion of sterilization. It may also include any additional steps between 60 and 70. Therefore, maintaining to achieve sterilization means maintaining the load in the chamber with the necessary steps to achieve sterilization.

After the sterilization process is complete, the current is shut off to the plasma generator, quenching the plasma, step 72 of FIG. 3. The chamber 12 is then vented to approximately atmospheric pressure through the HEPA vent 26 during the vent step 74 of FIG. 3. The pressure in the chamber during the venting step is shown by curve 76 of FIG. 4. The vent after the post-plasma stage helps to carry heat from the electrode and chamber walls to the instruments in the load. Very little heat is transferred from the electrode and chamber walls to the load during the post-plasma stage, curve 68 of FIG. 4, because the vacuum in the chamber does not effectively transfer heat. Venting the chamber allows for heat transfer from the electrode and chamber walls to the load.

The chamber is evacuated again in step 78 of FIG. 3, as shown as curve 80 of FIG. 4. The final evacuation removes sterilizing agent from the chamber. The chamber is preferably evacuated to a pressure less than or equal to 10,000 mTorr, more preferably to a pressure less than or equal to 5000 mTorr, and most preferably to a pressure less than or equal to 1000 mTorr. The heat which was transferred to the load during the vent step aids in removing the sterilizing agent from the load. Following this evacuation step, the chamber is again vented to atmospheric pressure through the HEPA vent 26, as indicated by curve 84 of FIG. 4. The sterilized articles are then removed from the chamber.

Figure 5:
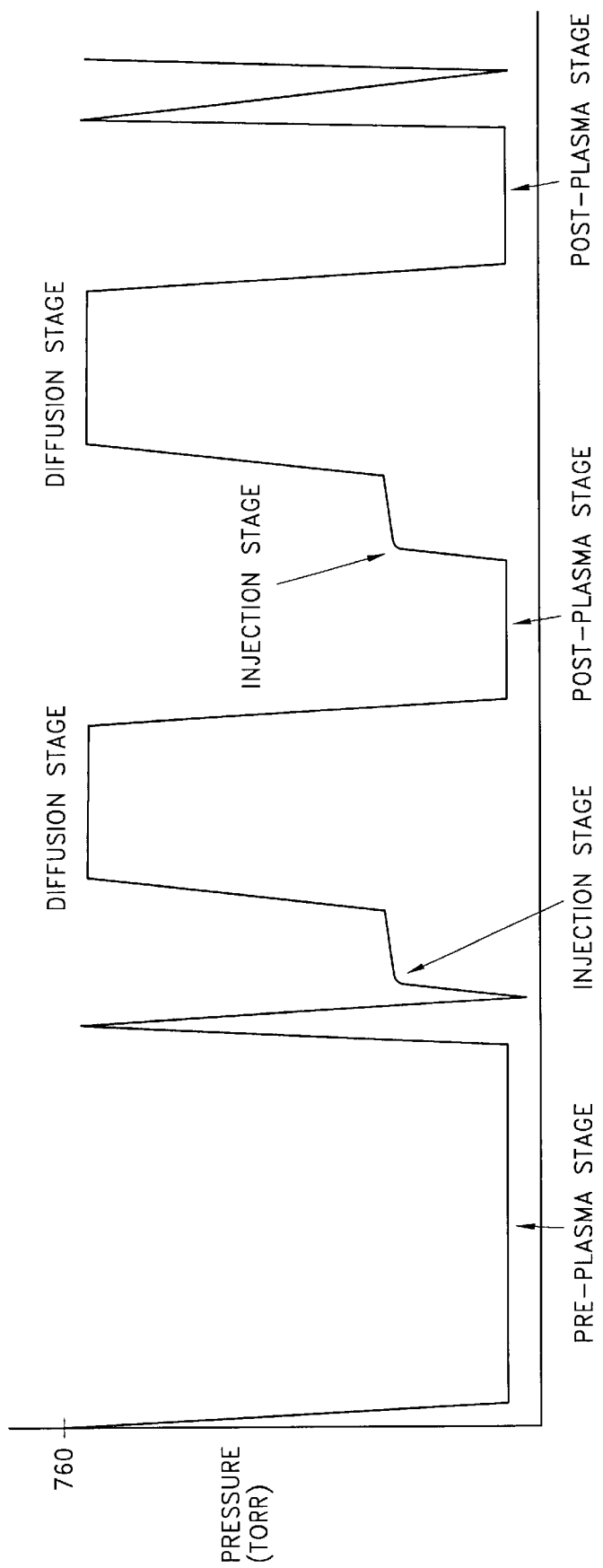
FIG. 5 is a pressure diagram of a "full cycle" sterilization process.

The cycle shown in FIG. 4 and described above has been termed a "half-cycle", which normally demonstrates sterile results to meet the regulatory requirements. Normally, the full sterilization cycle is longer than the half cycle to provide an additional sterility assurance level. The full cycle can be extended by doubling the sterilant exposure time or repeating the sterilization steps such as steps 52–72 in FIG. 3. In this embodiment, sterilizing agent is injected a second time after the post-plasma stage. In the full cycle, the sections of the curve labeled as 58, 61, 64, and 68 in FIG. 4, the injection, diffusion, evacuation, and post-plasma stages, are repeated after the post-plasma stage, curve 68, and before venting, curve 76, and evacuating, curve 80. In the "full cycle", therefore, the equipment to be sterilized is treated with sterilizing agent twice rather than once, as in the "half cycle". FIG. 5 shows a diagram of a full cycle.

Figure 6:
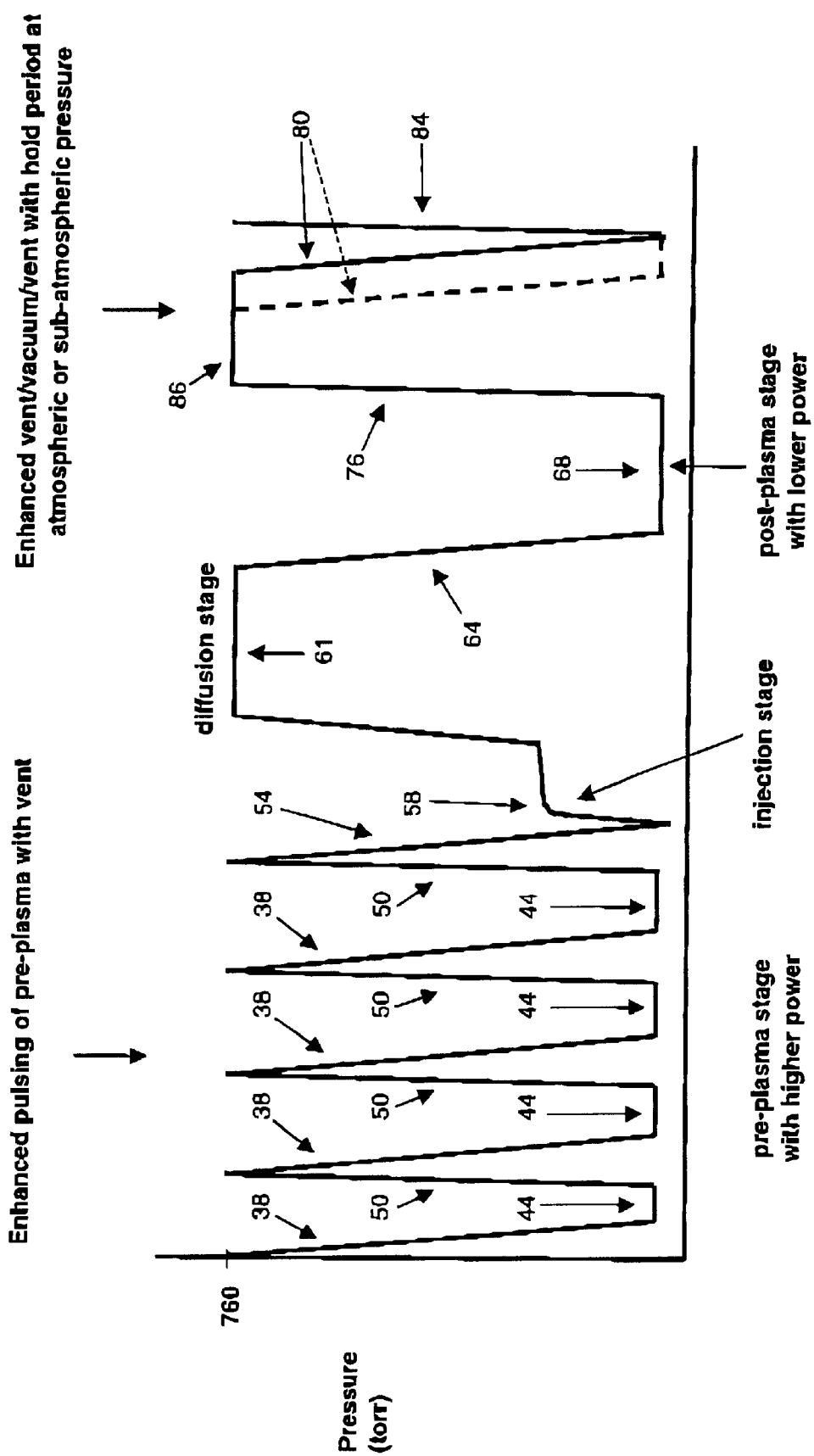
FIG. 6 is a pressure diagram of a sterilization process including enhancements for sterilization efficiency and improved material compatibility.

The enhanced sterilization method of the present invention is shown in FIG. 6 and will be described in detail below. Although many of the steps are similar to the method described above, there are enhancements to the pre-plasma stage, steps 36–48 of FIG. 2, the post-plasma process, steps 66–72 of FIG. 3, and the vent after the post-plasma stage, steps 74–82 of FIG. 3. Each of these enhancements will be discussed in turn, and the improvements in sterilization effectiveness and material compatibility that result from these improvements will be described through the Examples below. Although the same step numbers and curve numbers are used as in FIGS. 2–4, it is to be understood that the process conditions for some of the steps in the enhanced method are different than the process conditions employed in the method described in FIGS. 1–4. Further, some of the steps of the process of FIGS. 1–4 are repeated in the enhanced sterilization process shown in FIG. 6, and the enhanced process preferably contains a step which was not part of the process of FIGS. 2–4.

It is to be understood that each of the enhancements is an independent embodiment of the enhanced sterilization method, and it is not necessary to employ all of the enhancements to practice the invention. Although all of the enhancements are used in the preferred embodiment, each of the enhancements can be practiced separately or in combination with each other as embodiments of the invention.

As a brief introduction to the various embodiments of the enhanced sterilization method, the first enhancement is to alternately evacuate, treat with pre-plasma, and vent the chamber multiple times during the pre-plasma stage, as shown in FIG. 6. The pulsing of pre-plasma with venting has been found to improve the sterilization efficiency of the process. Although we do not wish to be tied to a theory as to why the pulsing improves the sterilization efficiency, it is believed that when the plasma is generated, the electrode and surrounding walls become hotter than the load, which is usually at ambient temperature when initially placed in the chamber. The multiple vents carry heat from the electrode and walls to the load to be sterilized. It is likely that the higher load temperature allows better evaporation of the chemical sterilant at subambient pressure when it is injected into the chamber later in the process, enhancing penetration to areas of close contact on the devices to be sterilized and achieving better sterilization lethality or sterilization efficiency. The venting pressure during the pre-plasma pulsing can be any pressure higher than the plasma-enhanced conditioning pressure. Also, the venting stage can have a holding period to enhance the heat transfer to the load. The effectiveness of the pulsing during the pre-plasma stage for enhancing the sterilization efficiency will be demonstrated in the Examples below. It is to be understood that other means of heat source can be employed to enhance heat transfer, such as a conventional heater or infrared lamp, with or without circulating means.

The second enhancement is to maintain the vent after the post-plasma stage for an extended period of time before evacuating, rather than evacuating immediately after reaching atmospheric pressure, as in curves 76 and 80 of FIG. 4. Maintaining the chamber at atmospheric pressure or subatmospheric pressure for an extended period of time has been found to reduce the residual level of sterilant on the sterilized devices.

Although we do not wish to be tied to a theory as to why maintaining the vent reduces the residual level of sterilant, it is likely that the extended vent gives more time for the heat from the hotter electrode and the chamber walls to be transferred to the load. One possible explanation for the reduced residual level is that the higher temperature of the load increases the volatility of the residual sterilant on the sterilized instruments, and subsequent exposure to vacuum is more effective at vaporizing the residual sterilant from the instruments. The effectiveness of the extended vent before evacuation in reducing residual levels of sterilant on the load will be demonstrated by the data in the Examples below.

Finally, the third enhancement of the invention is to use a lower RF power level to generate the plasma in the post-plasma stage than in the pre-plasma stage. Use of a lower power level in the post-plasma stage than in the pre-plasma stage has been found to improve the material compatibility while simultaneously maintaining high sterilization efficiency.

Without wishing to be tied to a theory for the reason for the improved material compatibility by using different RF levels, it seems likely that the improvement in material compatibility is due to the different reactivities of the plasmas formed in the pre-plasma stage and the post-plasma stage. The plasma in the pre-plasma stage is formed from air and moisture, and the plasma in the post-plasma stage is formed from a mixture of air and sterilization agent, normally hydrogen peroxide. The plasma formed from the mixture of air and sterilization agent is more reactive than the plasma formed from air and moisture. It is believed that a higher RF power level can be used in the pre-plasma stage than in the post-plasma stage without affecting material compatibility, because the pre-plasma plasma is less reactive.

The method for achieving enhanced sterilization while simultaneously maintaining good material compatibility will now be described in more detail.

Referring to the process of FIG. 6, the chamber 12 is evacuated as in step 36 of FIG. 2. The pressure curve for the evacuation is shown in FIG. 6 as curve 38. Steps 40, 42, 46, and 48 of FIG. 2 are then performed, striking the plasma, plasma enhanced conditioning, quenching the plasma, and venting. The period of time that the plasma is generated in the pre-plasma stage varies from 1 to 120 minutes, more preferably from 2–60 minutes, and most preferably 5–30 minutes. Up to this point, the process is essentially identical to the process shown in FIGS. 2–4.

In the enhanced method shown in FIG. 6, rather than injecting the reactive agent 18 after venting and evacuating, steps 36, 40, 42, 46, and 48 of FIG. 2 are repeated one or more times. In FIG. 6, the evacuation, plasma, vent process is repeated 4 times rather than occurring only once as in the process shown in FIG. 4. In FIG. 6, the pressure changes occurring in the pulsing process are shown as curves 38, 44, 50, 38, 44, 50, 38, 44, 50, 38, 44, 50, and 54. In preferred embodiments of the invention, steps 36, 40, 42, 46 and 48 of FIG. 2 can be repeated from 1 to 40 times, more preferably 2–10 times. In a preferred embodiment of the invention, the evacuation, plasma, vent, evacuation steps are repeated at least 2–5 times.

Each time plasma is generated, more heat is generated. It is believed that venting the chamber after generating the plasma transfers heat to the load to be sterilized, therefore conditioning the load. The higher temperature of the load could increase the volatility of the chemical sterilant when it is injected later in the process, improving the availability and penetration of the sterilant vapor. A possible explanation for the effectiveness of venting in improving the efficiency of sterilization is that increasing the temperature of at least a portion of the load to a temperature above ambient temperature has been found to lead to improved sterilization. More preferably, the temperature of at least a portion of the load is increased to 30° C. or more, and most preferably to 35° C. or more. The effectiveness of the pulsing in improving sterilization, the number of cycles which constitute a preferred number of cycles, and the preferred time length of the cycles will become clear in the Examples below.

After the final vent in the pre-plasma stage of the enhanced method, the chamber is evacuated to less than or equal to 10,000 mTorr, more preferably to 100–5000 mTorr, and most preferably to 300–1000 mTorr, step 52 of FIG. 3, the reactive agent is injected, step 56, the reactive agent is allowed to diffuse with or without a vent, step 60, and the chamber is evacuated, step 62. The pressure curves for these steps are shown as curves 54, 58, 61, and 64 in FIG. 6. This portion of the enhanced method is identical to the method shown in FIG. 4. It seems likely that the increased temperature of the load due to the pulsing in the pre-plasma stage increases the volatility of the sterilant, enhances the overall available sterilant concentration in the vapor phase, and improves the penetration and sterilization effectiveness of the sterilant vapor.

The next enhanced method takes place in step 66 of FIG. 3, where the plasma is generated in the post-plasma stage after the reactive agent has been injected, diffused, and the chamber has been evacuated. In the conventional sterilization method of FIGS. 2–4, the same power levels are used for the plasma in the pre-plasma of step 42 of FIG. 2 and the post-plasma of step 66 of FIG. 3. The two plasma treatments are also shown as curves 44 and 68 in FIG. 4 for the conventional method and FIG. 6 of the enhanced method.

It has been found that it is advantageous to generate plasma with a lower power level in the post-plasma treatment, step 66 of FIG. 3, than in the pre-plasma treatment, step 42 of FIG. 2. In the present embodiment, employing a lower power level of 100 to 600 Watts in the post-plasma treatment than the 300 to 1500 Watts of the pre-plasma treatment leads to improved material compatibility, as will be shown in the Examples below. It is to be understood that the power level is dependent on chamber size and design and that the post-plasma power levels should meet sterility requirements. The pre-plasma power can be higher to enhance the heat generation and transfer.

While we do not wish to be tied to a theory as to the reason for the improved material compatibility by using different power levels while generating the two forms of plasma, the plasma in the pre-plasma treatment is generated from air and moisture, while the plasma in the post-plasma treatment is generated with a mixture of air, moisture, and the reactive agent 18. The reactive agent is typically hydrogen peroxide and, or, other sterilants, and the plasma generated from chemical sterilant is more reactive than the plasma generated from air and moisture. It seems likely that use of a lower power level in the post-plasma stage than in the pre-plasma stage reduces damage to the materials inside the sterilization chamber due to the reactive plasma formed from the air/hydrogen peroxide in the chamber in the post-plasma stage. The lower power level in the post-plasma stage leads to improved material compatibility.

After the plasma in the post-plasma stage is quenched (step 72 of FIG. 3), the chamber 12 is vented, step 74 of FIG. 3 and curve 76 of FIG. 6. In the enhanced method of the present invention, the chamber 12 is held at approximately atmospheric pressure or subatmospheric pressure after the vent, an additional step 86, not shown on FIG. 3. The additional step takes place between the vent step 74 and the evacuate step 78 of FIG. 3. The pressure curve of the hold step is shown as 86 on FIG. 6. The vent, hold, evacuate curves are shown as curves 76, 86, and 80 of FIG. 6 and can be compared to curves 76 and 80 of FIG. 4, without the hold step. During the hold step, the pressure in the chamber is held at approximately atmospheric pressure or subatmospheric pressure for a period of 0.1 to 300 minutes, more preferably 1 to 60 minutes, and most preferably 1 to 20 minutes. Without wishing to be tied to a theory for the reason for the benefit, it seems likely that during the hold step, heat from the hotter electrode and the hotter walls can be transferred to the load, heating the load. It is believed that the higher temperature load increases the volatility of the residual sterilant on the instruments, leading to lower residual levels on the instruments when the chamber is evacuated after the hold step. Heating at least a portion of the load to a temperature above ambient temperature, more preferably to a temperature above 30° C., and most preferably to a temperature above 35° C. has been found to be effective in reducing the residual level of sterilant on the load. The reduced residuals on the sterilized equipment with the hold step and the preferred length of time for the hold step are shown in the Examples below.

The process can be repeated, with and without intermittent plasma before each vent to generate heat and further reduce process residuals.

To reduce cycle time, the combination of one vent and one pump down is desirable. To reduce process residuals, however, the process can be repeated, preferably with plasma generation before each vent to generate more heat to be transferred to the load.

After the hold step 86, the enhanced method is identical to the conventional method of FIG. 4. The chamber 12 is evacuated to subambient pressure, step 78 of FIG. 3, to a pressure of approximately 50 mTorr to 750 Torr, with the pressure curve 80 shown in FIG. 6. The chamber is vented again, step 82 of FIG. 3 and curve 84 of FIG. 6, and the sterilized equipment is removed from the chamber 12. Before the vent step 84, the pressure can be held at reduced pressure to enhance residual removal.

The enhancements to the method to improve sterilization and material compatibility therefore comprise the followings:

1. Repeated venting, evacuation and plasma treatment steps in the pre-plasma stage. Venting can be to atmospheric or subatmospheric pressure. The vent stage can have a holding period.
2. Use of a lower power level for the post-plasma stage than for the pre-plasma stage; and
3. After the post-plasma stage, holding the chamber at atmospheric pressure or sub-atmospheric pressure for a period of time after venting, before re-evacuating the chamber, rather than evacuating immediately after the chamber is vented to atmospheric pressure or subatmospheric pressure.

The unexpected benefits of these three enhancements in improving sterilization efficiency with improved material compatibility are demonstrated in the Examples below. The improved method can comprise one or more of the three enhancements, and it is not necessary to practice all three enhancements to obtain at least some of the benefits of enhanced sterilization with improved material compatibility.

The first set of examples demonstrates the improved sterilization obtained by repeated pulsing during the venting and plasma steps during the pre-plasma stage.

EXAMPLE 1

Effect of Multiple Venting Steps During the Pre-Plasma Stage

In the following example, stainless steel coupons inoculated with >$10^6$ *Bacillus stearothermophilus* spores were placed inside a 1 mm ID×2000 mm long polyethylene (PE) lumen, attached with a vessel containing liquid sterilant, 142 µL of 48% by weight aqueous hydrogen peroxide (U.S. Pat. No. 4,913,414). Placement of the inoculated coupon in the lumen was accomplished with a coupon holder (3 mm ID×15 mm long) located at approximately 1500 mm from the vessel containing the liquid sterilant. Lumens with the inoculated coupons were placed in each of the trays containing sets of various medical devices. The trays were wrapped with sterilization wrap, sealed with sterilization tape, placed within a 270 liter sterilization chamber and treated with various forms of the enhanced sterilization cycle shown in FIG. 6.

The sterilization chamber with the lumens and inoculated coupons was evacuated to 600 mTorr, plasma was generated for a total of 20 or 35 minutes with the RF setting shown in the Table below, the plasma was quenched, the chamber was vented to one atmosphere, and the chamber was evacuated to a pressure of 600 mTorr. At this point, in some experiments, one or more additional vent/evacuate/plasma cycles were performed, as shown in pressure curves 50, 38, and 44 of FIG. 6. The length of time in minutes for the pre-plasma treatments is shown as a numerical figure in bold in the second column of Table 1 below. The experiments with multiple bold figures are experiments in which multiple plasma/vent cycles were performed. If only one pre-plasma treatment was done, there is only a single bold number in the Table. The figure in bold indicates the number of minutes that plasma was generated for each cycle.

After the last pre-plasma treatment, the chamber was vented to one atmosphere, evacuated to 600 mTorr, 9.3 mg/L of 59% hydrogen peroxide was injected, increasing the pressure in the chamber to approximately 8000 mTorr. After the 6.5 minute injection step, the chamber was vented to one atmosphere pressure to allow the hydrogen peroxide to diffuse for 10 minutes, and the chamber was evacuated again to 600 mTorr. Plasma was generated in the post-plasma stage for a period of 2 minutes. In some cases, a different power level was used for the pre-plasma stage than for the post-plasma stage. If two different power levels were used, the first number in the third column of Table 1 is the RF level for the pre-plasma stage, and the second number is the RF level for the post-plasma stage.

After the post-plasma treatment, the chamber was vented to 1 atmosphere, evacuated to a pressure of 600 mTorr, and vented again to 1 atmosphere. No hold was used after the post-plasma vent. The lumens with inoculated coupons were removed from the chamber, and the inoculated coupons were tested for number of survivors/total tested as a measure of the effectiveness of the sterilization treatment.

In Example 1A and 1C, pre-plasma was generated for 35 minutes. In Examples 1B and 1D, the sterilization was carried out with four 5 minute pre-plasma treatments with vents to atmospheric pressure in between the pre-plasma treatments. The 35 minutes of pre-plasma in Examples 1A and 1C was the same time required for the four 5 minute pre-plasma pulses of Example 1B and 1C together with the time needed to evacuate before the pre-plasma pulses. The results are shown in Table 1 below.

TABLE 1

| Experiment | Cycle | Pre-Plasma/Post-Plasma (RF, Watts) | Results |
|---|---|---|---|
| 1A | 35\6.5/10/2 | 460/460 | 1/36 - Unacceptable |
| 1B | 5\5\5\5\6.5/10/2 | 460/460 | 0/36 - Acceptable |
| 1C | 35\6.5/10/2 | 460/380 | 1/30 - Unacceptable |
| 1D | 5\5\5\5\6.5/10/2 | 460/380 | 0/30 - Acceptable |

The single pre-plasma treatment of Examples 1A and 1C did not sterilize all the coupons, while the 4 pulse/vent treatment of Examples 1B and 1D was effective in sterilizing all of the coupons. The pulsing sterilization was therefore more effective than a single long plasma treatment followed by a vent. The results also indicate that 460 watts/380 watts is as efficacious as 460 watts/460 watts.

EXAMPLE 2

Comparison of Material Compatibility with High and Low Power Post-Plasma

In this experiment, material compatibility was tested by treating devices and materials which degrade relatively easily and which have distinct degradation characteristics in the specified sterilization environment.

The cycle of Example 1B was used with four 5 minute pre-plasma treatments with a vent in between the plasma treatments, 6.5 minutes of diffusion after introduction of the hydrogen peroxide, holding the vent during diffusion for 10 minutes, and 2 minutes of post-plasma.

To verify the cycle efficacy of a sterilizer, International Organization for Standardization (per ISO 14937) required the minimum process conditions be used, such that the cycle is tested at the minimum limits of sterilant and other process parameters that would enhance the cycle effectiveness (worst case scenario). Therefore, the plasma powers used in Example 1 should be considered as the low end power limits for the plasma stages. The actual power setting should be slightly higher to include the proper safety margins.

Similarly, International Organization for Standardization (per ISO 14937) required the material compatibility be tested at the maximum limits of sterilant concentration and process parameters that would constitute the worst case scenario for material compatibility. Since the energy level of the plasma would directly affect the energy level of free radicals which may cause surface degradation on materials, the maximum levels of plasma power within the safety margin should be used to evaluate the material compatibility. Considering the possible power ranges for the power levels used in Example 1, it was decided that 490 watts and 420 watts should be the worst case scenario power levels for the 460 watts and 380 watts, respectively.

The effect of plasma power on material compatibility was shown in Table 2. The two tests below differed from one another by having high power in both the pre-plasma and the post-plasma treatments in the first experiment, and high power level in the pre-plasma followed by a lower level in the post plasma treatment in the second experiment.

TABLE 2

Comparison of High and Low RF in Post-Plasma Treatment

| RF Power Combination | No. of Cycles to Failure (avg.) Adhesive | No. of Cycles to Failure (avg.) Medical Device |
|---|---|---|
| 490/490 | 8.3 | 10.3 |
| 490/420 | 12.6 | 15 |

The results in Table 2 above demonstrate that using a lower RF power level in the post-plasma treatment than in the pre-plasma treatment leads to improved material compatibility. Results in Table 1 and Table 2 demonstrate that acceptable efficacy and improved material compatibility can be achieved by setting the pre-plasma power higher, 475±15 watts, than the post-plasma power level, 400±20 watts.

The following experiments demonstrate the benefit of holding the pressure in the chamber at one atmosphere pressure after venting following the post-plasma treatment. The data in the following experiments demonstrate that maintaining the vent pressure at one atmosphere pressure in the vent after the post-plasma stage reduces the residual levels of sterilant on the sterilized instruments.

EXAMPLE 3

Effect of Vent/Hold/Vacuum After Post-Plasma Step for Residual Removal

In this example, residual levels of sterilant were measured as a function of the length of time of maintaining the pressure in the chamber at one atmosphere pressure before re-evacuating the chamber after venting after the post-plasma stage.

A segmented polyurethane was cut to defined dimensions was used as the test material. This material is known to be a high absorber of hydrogen peroxide. Sterilization test conditions as in Experiment 1D were used for this residual evaluation, with four 5 minute pre-plasma treatments with a vent in between the plasma treatments, 6.5 minutes of diffusion after introduction of the hydrogen peroxide, holding the vent during diffusion for 10 minutes, and 2 minutes of post-plasma. Additional steps were added after the sterilization steps to evaluate the method for enhancing the residual removal.

In Experiment 3A, the chamber was vented after the end of the sterilization. In Experiment 3B, the chamber was vented after the sterilization, and the vent was held for 10 minutes. In Experiment 3C, the chamber was vented after sterilization, immediately reevacuated for 10 minutes, and then vented again. In Experiment 3D, the chamber was vented after sterilization, the vent was held for 5 minutes, the chamber reevacuated for 5 minutes, and vented again. Determination of the residual was done by titration. The results are shown in Table 3.

TABLE 3

Effect of Maintaining Vent Pressure After Post-Plasma Step

| Experiment | Cycle | Pre-Plasma/Post-Plasma (RF, watts) | Results of Residual |
|---|---|---|---|
| 3A | Sterilization steps + Vent | 460/380 | 1581 ppm |
| 3B | Sterilization steps + Vent + 10 minute hold | 460/380 | 1125 ppm |
| 3C | Sterilization steps + Vent + 10 minute Vacuum + Vent | 460/380 | 1032 ppm |
| 3D | Sterilization steps + Vent + 5 minutes Hold + 5 minutes Vacuum + Vent | 460/380 | 862 ppm |

The post sterilization treatment lasted a total of 10 minutes for Experiments 3B, 3C, and 3D. The residual with Experiment 3D was the lowest, where the post sterilization treatment was a 5 minute hold, 5 minutes of vacuum, then vent. The next lowest residual was Experiment 3C, where the chamber was vented, exposed to 10 minutes of vacuum, then vented again. Venting and holding for 10 minutes in Experiment 3B led to a higher residual level than for Experiments 3C and 3D, where there was exposure to vacuum after the vent. The highest residual was obtained for Experiment 3A, where the chamber was vented after sterilization with no post sterilization treatment. The conclusion is that even holding the materials for 10 minutes after venting reduces the residual significantly over simple venting alone. It is believed that the 10 minute hold allows heat to be transferred from the walls of the chamber to the load. Evacuating the chamber after venting removes more residual than holding alone. The lowest residual level was obtained with a 5 minute hold, followed by 5 minutes of vacuum, followed by a vent. The combination of heat transfer by holding and removing the residual with vacuum was more effective than simple holding alone.

Various modifications and alterations of this invention will be apparent to those skilled in the art without departing from the scope and spirit of this invention. It should be understood that the invention is not limited to the embodiments disclosed therein, and that the claims should be interpreted as broadly as the prior art allows.

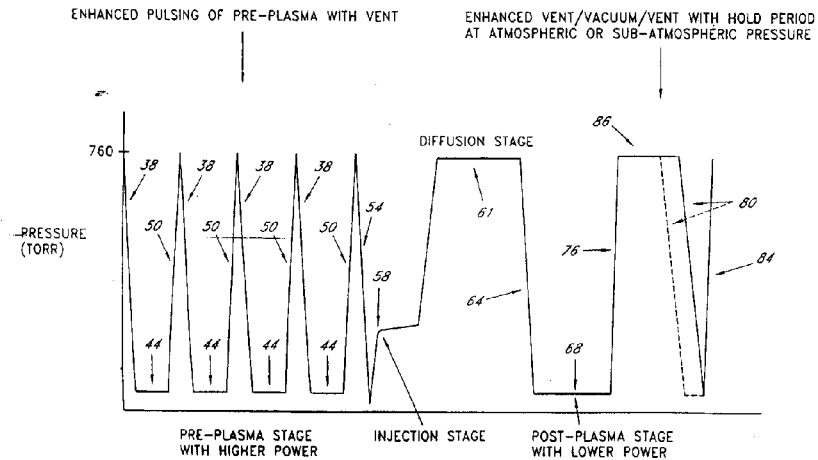

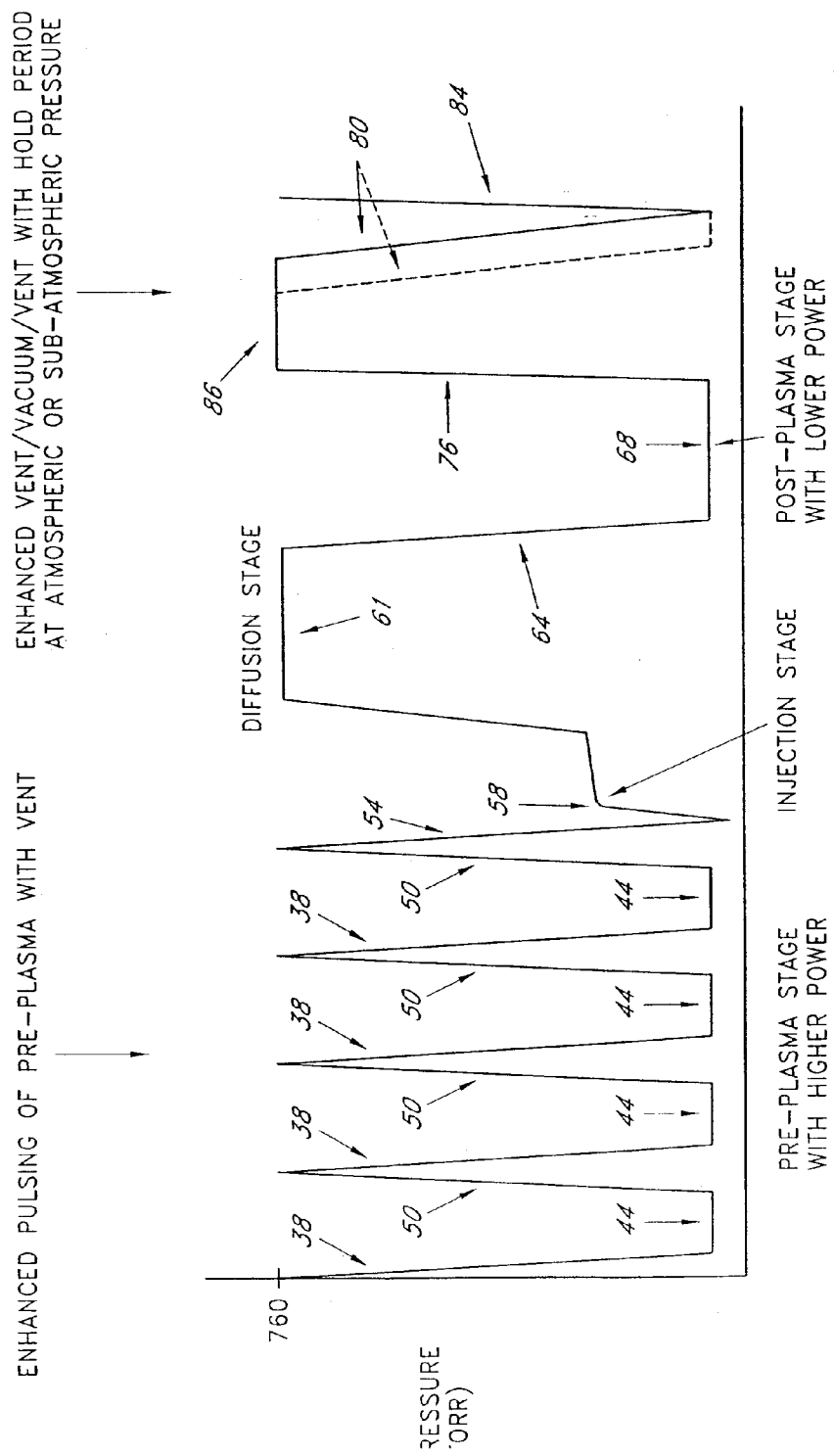

What is claimed is:

1. A method of sterilizing articles in a load in a chamber with a chemical sterilant, comprising:
   a) conditioning the load;
   b) introducing chemical sterilant;
   c) maintaining the load with the chemical sterilant to achieve sterilization,
   wherein conditioning the load comprises steps d) to g);
   d) evacuating said chamber;
   e) generating plasma in said chamber;
   f) venting said chamber to approximately atmospheric or subatmospheric pressure; and
   g) repeating d) to f) at least two times.

2. The method of claim 1, wherein conditioning the load comprises increasing the temperature of at least a portion of the load to at least 30° C.

3. The method of claim 1, wherein conditioning the load comprises increasing the temperature of at least a portion of the load to at least 35° C.

4. The method of claim 1, wherein said chemical sterilant comprises hydrogen peroxide.

5. The method of claim 1, additionally comprising venting said chamber to a pressure, maintaining said pressure, and then evacuating said chamber, wherein said venting is after step c).

6. The method of claim 1, wherein step b) or c) additionally comprises generating plasma in said chamber.

7. The method of claim 5, wherein the plasma is generated with lower power than the plasma of step e).

8. A method of reducing sterilant residuals on articles in a load in a chamber comprising:
   a) evacuating said chamber a first time;
   b) introducing sterilant;
   c) maintaining the load with the sterilant to achieve sterilization;
   d) venting said chamber to a pressure;
   e) maintaining said pressure;
   f) evacuating said chamber a second time;
   g) venting said chamber a second time; and
   h) removing said articles in said load from said chamber.

9. The method of claim 8, wherein said venting pressure is atmospheric or sub-atmospheric pressure.

10. The method of claim 8, additionally comprising generating plasma in said chamber in step b), c) or f).

11. The method of claim 8, further comprising repeating steps d) through f).

12. The method of claim 8, further comprising:
   a') evacuating said chamber;
   b') generating plasma in said chamber; and
   c') venting said chamber;
wherein steps a') to c') occur prior to steps a) to h) of claim 8.

13. A method for sterilizing devices in a chamber, said method having at least two plasma steps, wherein at least one plasma step occurs before introducing the chemical sterilant and at least one plasma step occurs after introducing said chemical sterilant, comprising:
   generating plasma with a higher power level in the at least one plasma step occurring before introducing the chemical sterilant than in the at least one plasma step occurring after introducing said chemical sterilant.

14. The method of claim 13, wherein said chemical sterilant comprises hydrogen peroxide.

15. The method of claim 13, additionally comprising:
   a) venting said chamber; and
   b) evacuating said chamber;
   wherein steps a) and b) occur after generating plasma with the higher power level.

16. The method of claim 13, additionally comprising:
   a) venting said chamber to a pressure;
   b) maintaining said pressure; and
   c) evacuating said chamber,
wherein steps a) through c) occur after the at least one plasma step occurring after introducing said chemical sterilant.

17. A method of sterilizing articles in a load with a chemical sterilant in a chamber with improved material compatibility comprising:
   a) evacuating the chamber;
   b) generating plasma with a first power level;
   c) venting the chamber to a pressure
   d) evacuating the chamber;
   e) introducing chemical sterilant into the chamber, wherein said introducing occurs after generating plasma with the first power level;
   f) evacuating the chamber;
   g) generating plasma with a second power level, wherein said generating plasma with the second power level occurs after said introducing;
   h) venting said chamber, wherein said venting occurs after generating plasma with the second power level;
   i) evacuating said chamber; and
   j) venting said chamber,
wherein said first power level is higher than said second power level, thereby sterilizing said articles with improved material compatibility.

18. The method of claim 17, additionally comprising repeating steps a), b) and c) more than once.

19. The method of claim 17, additional comprising venting after step e).

20. The method of claim 17, additionally comprising maintaining the pressure after venting step h).

21. The method of claim 17, additionally comprising generating plasma in said chamber after step i).

22. The method of claim 17, additionally comprising repeating steps h) and i).

23. The method of claim 17, wherein said chemical sterilant comprises an antimicrobial agent.

24. The method of claim 23, wherein said antimicrobial agent comprises hydrogen peroxide.

* * * * *

UNITED STATES PATENT AND TRADEMARK OFFICE
CERTIFICATE OF CORRECTION

PATENT NO.    : 6,365,102 B1
DATED         : April 2, 2002
INVENTOR(S)   : Wu et al.

It is certified that error appears in the above-identified patent and that said Letters Patent is hereby corrected as shown below:

Title page, should be deleted to be replaced with the attached title page.

Drawings,
The drawing sheet consisting of Fig. 6, should be deleted to be replaced with the drawing sheet, consisting of Fig. 6, as shown on the attached page.

Column 1,
Line 54, delete "arc", and insert -- are --.

Column 3,
Line 49, insert a period after the word "chamber".

Column 6,
Line 16, delete "dulling", and insert -- during --.

Column 10,
Line 20, delete "C.,", and insert -- C, --.
Line 21, delete "C.", and insert -- C --.

Column 12,
Table 1, lines 6 and 8, bold the numbers -- 35\ -- the the beginning of the number under the heading "Cycle."
Table 1, lines 7 and 9, bold the numbers -- 5\5\5\5\ -- at the beginning of the number under the heading "Cycle."

Signed and Sealed this

Twenty-second Day of April, 2003

JAMES E. ROGAN
*Director of the United States Patent and Trademark Office*

(12) United States Patent
Wu et al.

(10) Patent No.: US 6,365,102 B1
(45) Date of Patent: Apr. 2, 2002

(54) METHOD OF ENHANCED STERILIZATION WITH IMPROVED MATERIAL COMPATIBILITY

(75) Inventors: Su-Syin S. Wu, Irvine; Nancy S. Chu, Laguna Niguel; Abraham Merhazion, Tustin, all of CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

(21) Appl. No.: 09/470,246

(22) Filed: Dec. 22, 1999

Related U.S. Application Data

(60) Provisional application No. 60/127,160, filed on Mar. 31, 1999.

(51) Int. Cl.$^7$ .............................. A61L 2/14; A61L 2/16
(52) U.S. Cl. .............................. 422/23; 422/28; 422/33
(58) Field of Search ........................... 204/164; 422/23, 422/33, 186.05, 186.23, 186.25; 34/257

(56) References Cited

U.S. PATENT DOCUMENTS

| | | | |
|---|---|---|---|
| 2,972,196 A | | 2/1961 | Early et al. |
| 4,335,071 A | * | 6/1982 | Thornton ...................... 422/26 |
| 4,348,357 A | | 9/1982 | Bithell ........................ 422/22 |
| 4,643,876 A | | 2/1987 | Jacobs et al. .................. 422/23 |
| 4,756,882 A | | 7/1988 | Jacobs et al. .................. 422/23 |
| 4,818,488 A | | 4/1989 | Jacob ......................... 422/23 |
| 5,084,239 A | | 1/1992 | Moulton et al. ................ 422/22 |
| 5,186,893 A | | 2/1993 | Moulton et al. ................ 422/23 |
| 5,244,629 A | | 9/1993 | Caputo et al. ................. 422/22 |
| 5,288,460 A | | 2/1994 | Caputo et al. ................. 422/23 |
| 5,413,758 A | | 5/1995 | Caputo et al. ................. 422/22 |
| 5,527,508 A | | 6/1996 | Childers et al. ............... 422/33 |
| 5,645,796 A | | 7/1997 | Caputo et al. ................. 422/22 |
| 5,656,238 A | | 8/1997 | Spencer et al. ................ 422/23 |
| 5,869,000 A | | 2/1999 | DeCato ........................ 422/33 |
| 6,060,019 A | * | 5/2000 | Spencer et al. ................ 422/23 |

FOREIGN PATENT DOCUMENTS

EP   0 707 186 A1   4/1996   ............. F26B/5/00

OTHER PUBLICATIONS

A New Technology for Instrument Sterilization, Advanced Sterilization Products, Paul T. Jacobs, 1993.

* cited by examiner

Primary Examiner—Margaret G. Moore
Assistant Examiner—Michael J Feely
(74) Attorney, Agent, or Firm—Knobbe, Martens, Olson & Bear, LLP

(57) ABSTRACT

A method of enhanced sterilization with improved material compatibility. The following enhancements have been made. First, repeated venting, evacuation, and plasma treatments can be performed in the pre-plasma stage. Second, a lower power level can be used in the post-plasma stage than in the pre-plasma stage. Third, after the post-plasma stage, the chamber can be held at atmospheric pressure or sub-atmospheric pressure for a period of time after venting, before re-evacuating the chamber, rather than evacuating after the chamber is vented to atmospheric pressure or sub-atmospheric pressure. Any of the three enhancements may be used separately, and it is not necessary to practice all three enhancements to obtain at least some of the benefits of enhanced sterilization with improved material compatibility.

24 Claims, 6 Drawing Sheets